United States Patent [19]
Roberts et al.

[11] Patent Number: 5,369,114
[45] Date of Patent: Nov. 29, 1994

[54] BIPHENYLENE BRANCHED ALKYLENEOXY QUINOLINES

[75] Inventors: David A. Roberts, Congleton; Robert J. Pearce; Robert H. Bradbury, both of Wilmslow; Andrew P. Thomas, Congleton, all of England

[73] Assignee: Imperial Chemical Industries PLC, London, England

[21] Appl. No.: 101,104

[22] Filed: Aug. 3, 1993

Related U.S. Application Data

[63] Continuation of Ser. No. 697,145, May 8, 1991, abandoned.

[30] Foreign Application Priority Data

May 9, 1990 [GB] United Kingdom ............ 9010394.6

[51] Int. Cl.$^5$ ............................................. A61K 31/47
[52] U.S. Cl. ......................................... 514/312; 546/4; 546/153; 546/156
[58] Field of Search ............... 514/312; 546/153, 155, 546/156

[56] References Cited

U.S. PATENT DOCUMENTS

| | | | |
|---|---|---|---|
| 3,932,416 | 7/1976 | Bays et al. | 514/314 |
| 4,034,075 | 7/1977 | Bays et al. | 514/314 |
| 4,461,896 | 7/1984 | Portlock | 546/165 |
| 4,920,131 | 4/1990 | Huang et al. | 514/311 |
| 4,920,133 | 4/1990 | Huang et al. | 546/155 |
| 5,028,615 | 7/1991 | Huang et al. | 546/180 |
| 5,126,344 | 6/1992 | Roberts et al. | 514/248 |
| 5,130,318 | 7/1992 | Roberts et al. | 514/299 |
| 5,219,863 | 7/1993 | Roberts et al. | 514/312 |
| 5,227,387 | 7/1993 | Dreikorn et al. | 514/312 |
| 5,240,940 | 8/1993 | Arnold et al. | 514/312 |
| 5,246,944 | 9/1993 | Greenlee et al. | 514/312 |
| 5,296,484 | 3/1994 | Coghlan et al. | 514/312 |

FOREIGN PATENT DOCUMENTS

| | | |
|---|---|---|
| 0107095 | 5/1984 | European Pat. Off. . |
| 0326330 | 8/1989 | European Pat. Off. . |
| 0348155 | 12/1989 | European Pat. Off. . |
| 0412848 | 2/1991 | European Pat. Off. . |
| 2143526 | 2/1973 | France . |
| 2332731 | 3/1974 | Germany . |
| 1188364 | 4/1970 | United Kingdom . |
| 2234748 | 2/1991 | United Kingdom ................ 546/153 |

OTHER PUBLICATIONS

Proctor et al. Jour Chem. Soc. Perkins Trans. vol. 1, pp. 1803–1808 (1972).
Hauser, et al. Jour. Am. Chem Soc vol. 77 p. 2852 (1955).
Raya et al. Am. Jour. of Hypertension, vol. 4 3345–3405 (1991).
Youssefyeh, R. D., et al. (principal author Huang) *J. Med. Chem.* (1990), 33, 1186–1194.
Huang, R–C *J. Med. Chem.* (1990), 33, 1194–1200.
Physician's Desk Reference, Medical Economics, Montvale, N.J. vol. 46 pp. 2255–2258 (1992).

Primary Examiner—Donald G. Daus
Attorney, Agent, or Firm—Cushman, Darby & Cushman

[57] ABSTRACT

There are disclosed quinolines of the formula

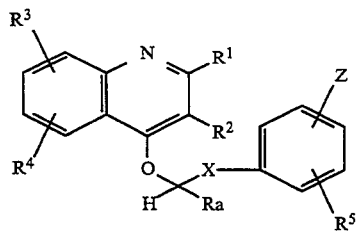

wherein $R^1$ is hydrogen, or hydrocarbyl. $R_3$ and $R_4$ are independently, H, alkyl, various functional groups or alkylenedioxy, X is phenylene optionally bearing a substituent, $R_a$ is (1–4)C alkyl optionally bearing one or more F's, Z is various carboxyl derivatives, useful as angiotensin II antagonists.

10 Claims, No Drawings

BIPHENYLENE BRANCHED ALKYLENEOXY QUINOLINES

This is a continuation of application No. 07/697,145, filed on May 8, 1991, which was abandoned upon the filing hereof.

This invention concerns novel heterocyclic compounds and, more particularly, novel quinoline derivatives which possess pharmacologically useful properties in antagonising at least in part one or more of the actions of the substances known as angiotensins, and in particular of that known as angiotensin II (hereinafter referred to as "AII"). The invention also concerns pharmaceutical compositions of the novel compounds for use in treating diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The invention also includes processes for the manufacture of the novel compounds and their use in treating one of the afore-mentioned diseases or medical conditions and for the production of novel pharmaceuticals for use in such medical treatments.

The angiotensins are key mediators of the renin-angiotensin-aldosterone system, which is involved in the control of homeostasis and fluid/electrolyte balance in many warm-blooded animals, including man. The angiotensin known as AII is produced by the action of angiotensin converting enzyme (ACE) from angiotensin I, itself produced by the action of the enzyme renin from the blood plasma protein angiotensinogen. AII is a potent spasmogen especially in the vasculature and is known to increase vascular resistance and blood pressure. In addition, the angiotensins are known to stimulate the release of aldosterone and hence result in vascular congestion and hypertension via sodium and fluid retention mechanisms. Hitherto there have been a number of different approaches to pharmacological intervention in the renin-angiotensin-aldosterone system for therapeutic control of blood pressure and/or fluid/electrolyte balance, including, for example, inhibiting the actions of renin or ACE. However, there remains a continuing need for an alternative approach because of the side-effects and/or idiosyncratic reactions associated with any particular therapeutic approach.

In our European Patent Application, Publication No. 412848 there are described certain quinoline derivatives having AII antagonist activity. Also certain structurally related quinoline derivatives are described in European Patent Application, Publication No. 348155 as being antagonists of leukotriene D4.

We have now discovered that the compounds of the invention (set out below) surprisingly antagonise one or more of the actions of the substances known as angiotensins (and in particular of AII) and thus minimise the physiological effects associated with their presence in warm-blooded animals (including man) and this is the basis of the invention.

According to the invention there is provided a quinoline derivative of the formula I (set out hereinafter, together with the other chemical formulae identified by Roman numerals) wherein $R^1$ is hydrogen, (1–8C)alkyl, (3–8C)cycloalkyl, phenyl or substituted (1–4C)alkyl, the latter containing one or more fluoro substituents or bearing a (3–8C)cycloalkyl, hydroxy, (1–4C)alkoxy or phenyl substituent; $R^2$ is hydrogen, (1–8C)alkyl, (3–8C)cycloalkyl, (3–8C)cycloalkyl-(1–4C)alkyl, carboxy, (1–4C)alkoxycarbonyl, cyano, nitro, phenyl or phenyl(1–4C)alkyl; $R^3$ and $R^4$ are independently selected from hydrogen, (1–4C)alkyl, (1–4C)alkoxy, fluoro(1–4C)alkoxy, halogeno, trifluoromethyl, cyano, nitro, hydroxy, amino, (1–4C)alkanoylamino, alkylamino and dialkylamino of up to 6 carbon atoms, dialkylamino-alkyl of 3 to 8 carbon atoms, (1–4C)alkanoyl, carbamoyl, N-alkylcarbamoyl and di-(N-alkyl)carbamoyl of up to 7 carbon atoms, carboxy, (1–4)alkoxycarbonyl, (1–6C)alkylthio, (1–6C)alkylsulphinyl, (1–6C)alkylsulphonyl, and substituted (1–4C)alkyl, the latter bearing an amino, hydroxy or (1–4C)alkoxy substituent; or $R^3$ and $R^4$ together form (1–4C)alkylenedioxy attached to adjacent carbon atoms of the benzene moiety of formula I; $R^5$ is hydrogen, (1–4C)alkyl, (1–4C)alkoxy, halogeno, trifluoromethyl, cyano or nitro; X is phenylene optionally bearing a substituent selected from (1–4C)alkyl, (1–4C)alkoxy, halogeno, trifluoromethyl, cyano and nitro; Ra is (1–4C)alkyl optionally bearing one or more fluoro substituents; Z is 1H-tetrazol-5-yl, -CO.NH.(1H-tetrazol-5-yl) or a group of the formula —CO.OR$^6$ or —CO.NH.SO$_2$.R$^7$ in which $R^6$ is hydrogen or a non-toxic, biodegradable residue of a physiologically acceptable alcohol or phenol, and $R^7$ is (1–6C)alkyl, (3–8C)cycloalkyl or phenyl; and wherein any of said phenyl moieties may be unsubstituted or bear one or two substituents independently selected from (1–4C)alkyl, (1–4C)alkoxy, halogeno, cyano and trifluoromethyl; or a non-toxic salt thereof.

It will be appreciated that, in compounds of the formula I, the carbon atom to which Ra is attached is asymmetric, and hence, depending on the nature of the other substituents present, compounds of the formula I will possess one or more chiral centres and will be isolated in one or more racemic or optically active forms. It is to be understood that this invention concerns any form of such a compound of formula I which possesses the afore-mentioned useful pharmacological properties, it being well known how to make optically active forms, for example by synthesis from suitable chiral intermediates, and how to determine their pharmacological properties, for example by use of the standard tests described hereinafter.

It is to be understood that generic terms such as "alkyl" include both straight and branched chain variants when the carbon numbers permit. However, when a particular radical such as "propyl" is given, it is specific to the straight chain variant, branched chain variants such as "isopropyl" being specifically named where intended. The same convention applies to other radicals.

A particular value for $R^1$ or $R^2$ when it is alkyl is, for example, methyl, ethyl, propyl, butyl, isobutyl, sec-butyl, pentyl or hexyl; and when it is cycloalkyl is, for example, cyclopropyl, cyclopentyl or cyclohexyl.

A particular value for $R^1$ when it is alkyl bearing one or more fluoro substitutents is, for example, fluoromethyl, trifluoromethyl, 2,2,2-trifluoroethyl or pentafluoroethyl; and when it is alkyl bearing a hydroxy, cycloalkyl, (1–4C)alkoxy or phenyl substituent is, for example, hydroxymethyl, 1-hydroxyethyl, 2-hydroxyethyl, cyclopropylmethyl, cyclopentylmethyl, cyclohexylmethyl, 2-methoxyethyl, 2-ethoxyethyl, benzyl, 1-phenylethyl or 2-phenylethyl.

A particular value for $R^2$ when it is cycloalkyl-alkyl is, for example, cyclopropylmethyl, cyclopentylmethyl, cyclohexylmethyl or 2-cyclopentyl-ethyl; when it is phenylalkyl is, for example, benzyl, 1-phenylethyl or 2-phenylethyl; and when it is alkoxycarbonyl is, for example, methoxycarbonyl, ethoxycarbonyl or propoxycarbonyl.

Appropriate values for $R^3$ $R^4$ $R^5$, or , or for an optional substituent which may be present on X, as defined above, include by way of example:

for alkyl: methyl and ethyl; for alkoxy: methoxy and ethoxy; for fluoroalkoxy: trifluoromethoxy, 2-fluoroethoxy, 2,2,2-trifluoroethoxy and 3,3,3-trifluoropropoxy; for halogeno: fluoro, chloro, bromo and iodo; for alkanoylamino: formamido, acetamido and propanamido; for alkylamino: methylamino, ethylamino and butylamino; for dialkylamino: dimethylamino, diethylamino and dipropylamino; for dialkylamino-alkyl: dimethylaminomethyl, 2-(dimethylamino)ethyl, 2-(diethylamino)ethyl and 3-(diethylamino)propyl; for alkanoyl: formyl, acetyl and butyryl; for N-alkylcarbamoyl: N-methyl and N-ethylcarbamoyl; for di(N-alkyl)carbamoyl: N,N-dimethylcarbamoyl and N,N-diethylcarbamoyl; for alkoxycarbonyl: methoxycarbonyl, ethoxycarbonyl or propoxycarbonyl; for alkylthio: methylthio, ethylthio and butylthio; for alkylsulphinyl: methylsulphinyl, ethylsulphinyl and butylsulphinyl; and for alkylsulphonyl: methylsulphonyl, ethylsulphonyl and butylsulphonyl; for alkyl bearing an amino, hydroxy or alkoxy substituent: hydroxymethyl, 1-hydroxyethyl, 2-hydroxyethyl, aminomethyl, 2-aminoethyl, 2-methoxyethyl and 2-ethoxyethyl; and alkylenedioxy: methylenedioxy and ethylenedioxy.

A particular value for Ra when it is (1-4C)alkyl is, for example, methyl, ethyl or propyl; and when it is (1-4C)alkyl bearing one or more fluoro substituents is, for example, fluoromethyl, trifluoromethyl, 2,2,2-trifluoroethyl or pentafluoroethyl.

A particular value for $R^6$ when it is a non-toxic, biodegradable residue of a physiologically acceptable alcohol or phenol is, for example, a residue derived from a (1-6C)alkanol such as methanol or ethanol, or phenol, glycerol or the like.

A particular value for $R^7$ when it is alkyl is, for example, methyl, ethyl, propyl, isopropyl, butyl or pentyl; and when it is cycloalkyl is, for example, cyclobutyl, cyclopentyl or cyclohexyl.

Particular values for optional substituents which may be present on phenyl moieties include, by way of example, for halogeno: fluoro, chloro and bromo; for alkyl: methyl and ethyl; and for alkoxy: methoxy and ethoxy.

A specific value for X which is of particular interest is, for example, p-phenylene.

A preferred value for $R^6$ is, for example, hydrogen and for $R^1$ is, for example, methyl, ethyl or propyl.

A preferred value for $R^2$, $R^3$, $R^4$ or $R^5$ is for example hydrogen.

A preferred value for Ra is, for example, (1-4C)alkyl, particularly methyl.

A preferred group of compounds of the invention comprises those compounds of the formula Ia (set out hereinafter) wherein $R^1$, $R^2$, $R^3$, $R^4$, $R^5$ and Ra have any of their meanings as defined above and $Z^1$ is carboxy, 1H-tetrazol-5-yl or benzenesulphonamido, the latter optionally containing one or two substituents independently selected from halogeno (such as fluoro, chloro or bromo), (1-4C)alkyl (such as methyl or ethyl), (1-4C)alkoxy (such as methoxy or ethoxy), cyano, nitro and trifluoromethyl; together with the non-toxic salts thereof.

A preferred value for Z or $Z^1$ is, for example, carboxy or 1H-tetrazol-5-yl, which latter is especially preferred and, in particular, when it is attached ortho to the phenylene group X.

Compounds of the invention which are of particular interest include, for example, the specific embodiments set out hereinafter in the accompanying Examples, and these are provided, together with their non-toxic salts, as a further feature of the invention.

Although all of the formula I compounds can form salts with suitable acids, it will be appreciated that those compounds of formula I wherein Z is other than an ester group or in which $R^3$ or $R^4$ bear a carboxy group can form salts with bases as well as with acids. Particularly suitable non-toxic salts for such compounds therefore also include, for example, salts with bases affording physiologically acceptable cations, for example, alkali metal (such as sodium and potassium), alkaline earth metal (such as magnesium and calcium), aluminium and ammonium salts., as well as salts with suitable organic bases, such as with ethanolamine, methylamine, diethylamine or triethylamine, as well as salts with acids forming physiologically acceptable anions, such as salts with mineral acids, for example with hydrogen halides (such as hydrogen chloride and hydrogen bromide), sulphuric and phosphoric acid, and with strong organic acids, for example with p-toluenesulphonic and methanesulphonic acids.

The compounds of formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise:

a) For those compounds in which Z is carboxy (that is in which Z is a group of the formula —CO.OR$^6$ in which R$^6$ is hydrogen), a carboxylic acid derivative of the formula II, in which Q is a protected carboxy group selected from (1-6C)alkoxycarbonyl (especially methoxy-, ethoxy-, propoxy- or t-butoxy-carbonyl), phenoxycarbonyl, benzyloxycarbonyl and carbamoyl, is converted to carboxy.

The conversion may be carried out, for example by hydrolysis, conveniently in the presence of a suitable base such as an alkali metal hydroxide, for example, lithium, sodium or potassium hydroxide. The hydrolysis is generally carried out in the presence of a suitable aqueous solvent or diluent, for example in an aqueous (1-4C)alkanol, such as aqueous methanol or ethanol. However, it may also be performed in a mixture of an aqueous and non-aqueous solvent such as water and toluene using a conventional quaternary ammonium phase tranfer catalyst. The hydrolysis is generally performed at a temperature in the range, for example, 0°-120° C., depending on the reactivity of the group Q. In general, when Q is carbamoyl, temperatures in the range, for example, 40°-120° C. are required to effect the hydrolysis.

Alternatively, when Q is benzyloxycarbonyl, the conversion may also be performed by hydrogenolysis, for example using hydrogen at 1-3 bar in the presence of a suitable catalyst, such as palladium on charcoal or on calcium sulphate, in a suitable solvent or diluent such as a (1-4C)alkanol (typically ethanol or 2-propanol) and at a temperature in the range, for example, 0°-40° C.

Further, when Q is t-butoxycarbonyl, the conversion may also be carried out by hydrolysis at a temperature in the range, for example, 0°-100° C., in the presence of a strong acid catalyst, such as trifluoroacetic acid. The hydrolysis may either be performed in an excess of the acid or in the presence of a suitable diluent such as tetrahydrofuran, t-butyl methyl ether or 1,2-dimethoxyethane.

b) For those compounds of formula I wherein Z is tetrazolyl, a compound of the formula III in which L is a suitable protecting group, such as trityl, benzhydryl, trialkyltin (for example trimethyltin or tributyltin) or triphenyltin, affixed to a nitrogen of the tetrazolyl moiety, is deprotected.

The reaction conditions used to carry out the deprotection necessarily depend on the nature of the group L. As an illustration, when it is trityl, benzhydryl, trialkyltin or triphenyltin, the decomposition conditions include, for example, acid catalysed hydrolysis in a mineral acid (such as aqueous hydrochloric acid), conveniently in an aqueous solvent (such as aqueous dioxan or 2-propanol). Alternatively, a trityl or benzhydryl group may be removed by hydrogenolysis, for example as described in (a) above for conversion of a benzyloxycarbonyl to a carboxy.

Compounds of the formula III wherein L is trialkyltin or triphenyltin may be obtained, for example, by reaction of a nitrile of the formula XI with a trialkyltin azide, such as trimethyltin azide, or triphenyltin azide respectively. The reaction is conveniently carried out in a suitable solvent or diluent, such as toluene or xylene, and at a temperature in the range, for example, 50°-150° C. In a modified procedure, a formula I compound wherein Z is tetrazolyl may be obtained directly by in situ removal of the trialkyltin or triphenyltin group without prior isolation of the formula III compound, for example by the addition of aqueous mineral acid or gaseous hydrogen chloride to the reaction mixture. The nitriles of the formula XI may be obtained, for example, by reaction of a quinoline derivative of the formula VII wherein $Y^1$ is a suitable leaving group, such as chloro, bromo, iodo, methanesulphonyloxy or p-toluenesulphonyloxy, with an alcohol of the formula XII, using similar conditions to those used in process (d) described hereinafter. Alternatively the nitriles of formula XI may be obtained by conversion of the hydroxyl group of a compound of formula XII into a suitable leaving group such as a halogeno, methanesulphonyloxy or toluenesulphonyloxy group, for example by halogenation, mesylation or tosylation using standard conditions, followed by reaction of the resultant compound with a quinolone of the formula IV, using similar conditions to those described in process (c) hereinafter. As a yet further alternative, the nitriles of the formula XI may be obtained from stepwise conversion of a compound of formula I wherein Z is a group of the formula —CO.$OR^6$ under standard conditions. The alcohols of the formula XII may be obtained, for example, by an analogous procedure to that illustrated in Scheme 1 for the preparation of compounds of the formula IX but starting, for example, from the appropriate (bromomethyl)biphenylcarbonitrile itself obtained, for example, as illustrated in Scheme 2.

Alternatively, compounds of the formula III may be obtained, for example, by reaction of a quinoline of the formula VII wherein $Y^1$ is a suitable leaving group (such as chloro, bromo, iodo, methanesulphonyloxy or p-toluenesulphonyloxy) with an alcohol of the formula IX under similar conditions to those described in process (d) hereinafter. The alcohols of the formula IX may be obtained, for example, from the corresponding aldehydes of formula X by reaction with an alkali metal alkane of the formula Ra.M (such as methyllithium) or a reagent of the formula Ra.Mg.$X^2$ (a Grignard reagent) or Ra.Zn.$X^2$ wherein $X^2$ is halogeno, in the presence of an inert solvent or diluent such as tetrahydrofuran or diethyl ether or a mixture thereof, and at a temperature in the range $-80°$ to 25° C. The aldehydes of the formula X may be obtained, for example, by standard procedures such as those shown in Scheme 1. It will be appreciated that other well known reagents and conditions may be used for carrying out the steps of Scheme 1 to obtain an aldehyde of formula X, dependent on the nature of the protecting group L. For example, conventional hydrolyric conditions may be used for step (b) instead of reductive conditions.

c) A quinolone of the formula IV wherein $R^1$ is other than hydrogen is alkylated with a compound of the formula V wherein Hal. stands for a suitable leaving group such as chloro, bromo, iodo methanesulphonyloxy of p-toluenesulphonyloxy.

The reaction is generally carried out in the presence of a suitable base, for example, an alkali metal alkoxide such as sodium mathoxide or sodium ethoxide or an alkali metal hydride such as sodium hydride or an organic base such as diisopropylethylamine and in a suitable solvent or diluent, for example, a (1-4C)alkanol such as methanol or ethanol when an alkali metal alkoxide is used, or in a polar solvent such as N,N-dimethylformamide and at a temperature in the range, for example, 10°-100° C. Alternatively, a quaternary ammonium hydroxide may be used in a mixture of an aqueous and non-aqueous solvent such as water and dichloromethane. In carrying out process (c), when in the starting material Z is an acidic group, about two molecular equivalents of a suitable base is generally required, whereas when Z is a non-acidic group the presence of one molecular equivalent of a suitable base is generally sufficient.

Procedure (c) is particularly suitable for the production of those compounds of the formula I in which Z is a group of the formula —CO.$OR^6$ in which $R^6$ is other than hydrogen, for example wherein $R^6$ is (1-6C)alkyl, benzyl or phenyl, which compounds are also starting materials of formula II for the reaction described in (a) above. Similarly, using an analogous procedure, but starting with the appropriate compound of the formula VI, the starting materials of the formula III may be obtained for procedure (b).

Alternatively, a quinolone of the formula IV may be reacted with an alcohol of the formula VIII, for example in the presence of triphenylphosphine and diethylazodicarboxylate (DEAD). This may conveniently be carried out in a suitable solvent or diluent such as diethyl ether, tetrahydrofuran or dichloromethane, and at a temperature in the range of $-10°$ to 40° C.

The majority of the quinolones of formula IV are already known and the remainder can be made by analogy therewith using standard procedures of organic chemistry well known in the art, for example as described in standard works of heterocyclic chemistry such as that edited by Elderfield or in our European Patent Application, Publication No. 412848. The necessary compounds of the formula V may be made by standard procedures such as halogenation, mesylation or tosylation of a compound of formula VIII wherein Z is a group of the formula —CO.OR$^6$. Formula VI compounds may be obtained by a similar procedure starting from a compound of the formula IX.

The starting material for Scheme 1 and related compounds may also be conveniently obtained by reaction of a Grignard reagent, formed from a suitably substituted 4-bromotoluene, with a trialkyltin halide, such as tributyltin chloride, followed by reaction of the resulting (substituted)phenyltrialkyltin compound with a bromobenzonitrile in the presence of a palladium(O) catalyst, such as tetrakis(triphenylphosphine)palladium, and azo(bisisobutyronitrile). The resultant substituted 4'-methyl-biphenylcarbonitrile may then be converted to the said starting material by carrying out steps (b), (c) and (d) in a similar manner to that shown in Scheme 2. Alternatively, suitably substituted 4'-methylbiphenylcarbonitriles may be obtained by reaction of 4-methylphenylboronic acid with an appropriately substituted bromobenzonitrile in the presence of a suitable palladium catalyst, such as palladium (II)chloride or tetrakis(triphenylphosphine)palladium, and azo(-bisisobutyronitrile).

d) A quinoline derivative of the formula VII wherein Y$^1$ is a suitable leaving group (such as chloro, bromo, iodo, methanesulphonyloxy or p-toluenesulphonyloxy) is reacted with an alcohol of the formula VIII.

The reaction is generally carried out in the presence of a suitable base, for example an alkali metal alkoxide such as sodium methoxide or ethoxide or an alkali metal hydride such as sodium hydride and in a suitable solvent or diluent, for example a (1–4C)alkanol such as methanol or ethanol when an alkali metal alkoxide is used, or a polar solvent such as N,N-dimethylformamide. Alternatively, an alcohol of the formula VIII may be used in the form of its preformed alkali metal salt (when Z is a non-acidic group) or di-alkali metal salt (when Z is an acidic group). The reaction is usually performed at a temperature in the range of 40° to 120° C. The reaction may in preference be carried out in the presence of an acid catalyst such as p-toluenesulphonic acid, instead of under basic conditions, and in the presence of an inert solvent or diluent such as toluene.

The quinoline derivatives of the formula VII may be obtained, for example, by halogenation of the corresponding quinolones of formula IV, for example, by reaction with phosphorus oxychloride in the absence of a solvent, or in the presence of an inert solvent or diluent such as toluene or dioxane, and at a temperature in the range 60° to 110° C. The alcohols of the formula VIII may be obtained, for example, by an analogous procedure to that illustrated in Scheme 1 for the preparation of compounds of the formula IX but starting, for example, from the appropriate bromomethyl compound itself obtained, for example, as illustrated in Scheme 2 or by analogy therewith.

Whereafter, those compounds of formula I wherein Z is 1H-tetrazol-5-yl may be obtained by stepwise conversion of a compound of the formula I wherein Z is a group of the formula —CO.OR$^6$ into the corresponding nitrile under standard conditions, followed by reaction of the nitrile with an azide such as an alkali metal azide, preferably in the presence of an ammonium halide, and preferably in the presence of a suitable polar solvent such as N,N-dimethylformamide and at a temperature in the range, for example, 50° to 160° C.

Whereafter, those compounds of the formula I wherein Z is —CO.NH.(1H-tetrazol-5-yl) a group of the formula —CO.NH.SO$_2$R$^7$ or a group of the formula —CO.OR$^6$ in which R$^6$ is other than hydrogen, may be obtained, for example, by reacting a carboxylic acid of the formula I in which Z is carboxy (or a reactive derivative of said acid) with 5-aminotetrazole a sulphonamide of the formula NH$_2$.SO$_2$R$^7$ or a salt thereof (for example, an alkali metal salt), or a hydroxy compound of the formula HO.R$^6$ or with a salt thereof (for example, an alkali metal thereof). Suitable reactive derivatives include, for example the chloride, bromide, azide, anhydride and mixed anhydride with formic or acetic acid of the carboxylic acid of formula I as defined above. When the free acid form is used, the reaction is generally carried out in the presence of a suitable dehydrating agent such as dicyclohexycarbodiimide or 3-(3-dimethylaminopropyl)-1-ethylcarbodiimide in the presence of a base such as triethylamine or pyridine. When a reactive derivative is used, either the reaction is carried out in the presence of a base such as mentioned above, or, for the preparation of a compound of the formula I wherein Z is a group of the formula —CO.NM.SO$_2$R$^7$ or a group of the formula —CO.OR$^6$, the sulphonamide or hydroxy compound is used in the form of a salt, such as its alkali metal salt (in particular the lithium, sodium or potassium salt thereof). The reaction is generally performed in the presence of a suitable diluent or solvent such as dioxan, t-butyl methyl ether or tetrahydrofuran and at a temperature in the range, for example, 0°–60° C.

Whereafter, when a non-toxic salt of a compound of formula I is required, it may be obtained, for example, by reaction with the appropriate base affording a physiologically acceptable cation, or with the appropriate acid affording a physiologically acceptable anion, or by any other conventional salt formation procedure.

Further, when an optically active form of a compound of formula I is required, one of the aforesaid processes may be carried out using an optically active starting material. Alternatively, the racemic form of a compound of formula I in which Z is an acidic group may be resolved, for example by reaction with an optically active form of a suitable organic base, for example, ephedrine, N,N,N-trimethyl-(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure, for example using an aqueous mineral acid such as dilute hydrochloric acid.

Certain of the intermediates defined herein are novel, for example the compounds of the formula II and III, and are provided as a further feature of the invention.

As stated above, the compounds of formula I will have beneficial pharmacological effects in warm-blooded animals (including man) in diseases and medical conditions where amelioration of the vasoconstrictor and fluid retaining properties of the renin-angiotensin-aldosterone system is desirable, at least in part by antagonism of one or more of the physiological actions of AII. The compounds of the invention will thus be useful in the treatment of diseases or medical conditions such as hypertension, congestive heart failure and/or hyperaldosteronism in warm-blooded animals (including man), as well as in other diseases or medical conditions in which the renin-angiotensin-aldosterone system plays a significant causative role.

The antagonism of one or more of the physiological actions of AII and, in particular, the antagonism of the interaction of AII with the receptors which mediate its effects on a target tissue, may be assessed using one or more of the following, routine laboratory procedures:

Test A

This in vitro procedure involves the incubation of the test compound initially at a concentration of 100 micromolar (or less) in a buffered mixture containing fixed concentrations of radiolabelled AII and a cell surface membrane fraction prepared from a suitable angiotensin target tissue. In this test, the source of cell surface membranes is the guinea pig adrenal gland which is well known to respond to AII. Interaction of the radiolabelled AII with its receptors (assessed as radiolabel bound to the particulate membrane fraction following removal of unbound radiolabel by a rapid filtration procedure such as is standard in such studies) is antagonized by compounds which also bind to the membrane receptor sites and the degree of antagonism (observed in the test as displacement of membrane-bound radioactivity) is determined readily by comparing the receptor-bound radioactivity in the presence of the test compound at the specified test concentration with a control value determined in the absence of the test compound. Using this procedure compounds showing at least 50% displacement of radiolabelled AII binding at a concentration of $10^{-4}$ M are retested at lower concentrations to determine their potency. For determination of the $IC_{50}$ (concentration for 50% displacement of radiolabelled AII binding), concentrations of the test compound are ordinarily chosen to allow testing over at least four orders of magnitude centred about the predicted approximate $IC_{50}$, which latter is subsequently determined from a plot of percentage displacement against concentration of the test compound.

In general, acidic compounds of formula I as defined above show significant inhibition in Test A at a concentration of 50 micromolar or much less.

Test B

This in vitro test involves the measurement of the antagonistic effects of the test compound against AII-induced contractions of isolated rabbit aorta, maintained in a physiological salt solution at 37° C. In order to ensure that the effect of the compound is specific to antagonism of AII, the effect of the test compound on nonadrenaline-induced contractions may also be determined in the same preparation.

In general, acidic compounds of formula I as defined above show significant inhibition in Test B at a final concentration of 50 micromolar or much less. [Note: Compounds of formula I wherein Z is a group of the formula —CO.OR$^6$ in which R$^6$ is other than hydrogen in general show only weak activity in the in vitro Tests A or B.]

Test C

This in vivo test involves using terminally-anaesthetised or conscious rats in which an arterial catheter has been implanted under anaesthesia for the measurement of changes in blood pressure. The AII antagonistic effects of the test compound following oral or parenteral administration, are assessed against angiotensin II-induced pressor responses. To ensure that the effect is specific, the effect of the test compound on vasopressin-induced pressor responses may also be determined in the same preparation.

The compounds of formula I generally show specific AII-antagonist properties in Test C at a dose of 50 mg/kg body weight or much less, without any overt toxicological or other untoward pharmacological effect.

Test D

This in vivo involves the stimulation of endogenous AII biosynthesis in a variety of species including rat, marmoset and dog by introducing a diet of low sodium content and giving appropriate daily doses of a saluretic known as frusemide. The test compound is then administered orally or parenterally to the animal in which an arterial catheter has been implanted under anaesthesia for the measurement of changes in blood pressure.

In general compounds of formula I will show AII-antagonist properties in Test D as demonstrated by a significant reduction in blood pressure at a dose of 50 mg/kg body weight or much less, without any overt toxicological or other untoward pharmacological effect.

By way of illustration of the angiotensin II inhibitory properties of compounds of formula I, the compound of Example 1 gave the following results in tests A and C described above:

In test A: an $IC_{50}$ of $4 \times 10^{-8}$M;
In test C: $ED_{50}$ of 0.18 mg/kg (i.v. administration)

The compounds of formula I will generally be administered for therapeutic or prophylactic purposes to warm-blooded animals (including man) requiring such treatment in the form of a pharmaceutical composition, as is well known in the pharmaceutical art. According to a further feature of the invention there is provided a pharmaceutical composition comprising a compound of formula I, or a salt thereof as defined above, together with a pharmaceutically acceptable diluent or carrier. Such compositions will conveniently be in a form suitable for oral administration (e.g. as a tablet, capsule, solution, suspension or emulsion) or parenteral administration (e.g. as an injectable aqueous or oily solution, or injectable emulsion).

The compounds of formula I may also be advantageously administered for therapeutic or prophylactic purposes together with another pharmacological agent known in the general art to be of value in treating one or more of the diseases or medical conditions referred to hereinabove.

In general a compound of formula I (or a pharmaceutically acceptable salt thereof as appropriate) will generally be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or medical condition being treated according to principles well known in the medical arts.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will generally be administered in an analogous amount and manner to those described above for administration to humans. The compounds of formula I are also of value as pharmacological tools in the development and standardisation of test systems for the evaluation of the effects of AII in laboratory animals such as cats, dogs, rabbits, monkeys, rats and mice, as part of the continuing search for new and improved therapeutic agents.

The invention will now be illustrated by the following non-limiting Examples in which, unless otherwise stated:

(i) concentrations and evaporations were carried out by rotary evaporation in vacuo;

(ii) operations were carried out at room temperature, that is in the range 18°–26° C.;

(iii) flash column chromatography was performed on Merck Kieselgel 60 (Art. no. 9385) obtained from E Merck, Darmstadt, Germany;

(iv) yields, where given, are intended for the assistance of the reader only and are not necessarily the maximum attainable by diligent process development;

(v) $^1$H NMR spectra were normally determined at 200 MHz in CDCl$_3$ or d$_6$-dimethylsulphoxide (d$_6$-DMSO) using tetramethylsilane (TMS) as an internal standard, and are expressed as chemical shifts (delta values) in parts per million relative to TMS using conventional abbreviations for designation of major peaks: s, singlet; m, multipict; t, triplet; br, broad; d,doublet;

(vi) $^{13}$C NMR spectra were normally determined at 100 MHz in CDCl$_3$ or d$_6$-DMSO using the solvent signal as internal standard, and are expressed as chemical shifts (delta values) in parts per million relative to TMS; and (vii) all end-products had satisfactory microanalyses.

EXAMPLE 1

Concentrated hydrochloric acid (0.5 ml) was added to a solution of 2-methyl-4-[1-(2'-(2-triphenylmethyl-2H-tetrazol-5-yl)-biphenyl-4-yl)ethoxy]quinoline (A) (320 mg) in a mixture of ethanol (2 ml) and methanol (1 ml). The solution was left to stand for 3 hours. The precipitated solid was collected by filtration and washed with ether to give 2-methyl-4-[1-(2'-(1H-tetrazol-5-yl)biphenyl-4-yl)ethoxy]quinoline hydrochloride (120 mg), as a white solid, m.p. 168°–169° C.; NMR (d$_6$-DMSO): 1.8(d, 3H), 2.9(s, 3H), 6.2(q, 1H), 7.2(d, 2H), 7.45(s, 1H), 7.5–7.6(complex m, 4H), 7.65(d, 2H), 7.85(t, 1H), 8.1(t, 1H), 8.2(d, 1H), 8.45(d, 1H); mass spectrum (−ve FAB, DMSO/glycerol (GLY)): 406(M-H)$^-$, 248,158,127; microanalysis, found: C, 66.5; H,5.1; N, 15.8; H$_2$O 2.1%; C$_{25}$H$_{21}$N$_5$O.HCl.0.5 H$_2$O requires: C, 66.3; H, 5.1; N, 15.5; 2.0%.

The starting material (A) was obtained as follows:

(i) Powdered potassium acetate (17.5 g) was added to a solution of 5-[2-(4'-bromomethylbiphenylyl)]-2-triphenylmethyl-2H-tetrazole (50 g) (obtained as described in European Patent Application, Publication No. 0291969) and 1,4,7,10,13,16-hexaoxacyclooctadecane (100 mg) in 1,2-dimethoxyethane (DME)(600 ml), and the mixture was heated under reflux for 20 hours. Insoluble material was removed by filtration, and the residue triturated with a mixture of ethyl acetate and hexane (1:4 v/v) to give 5-[2-(4'-acetoxymethylbiphenylyl)]-2-triphenylmethyl-2H-tetrazole (B) (41.8 g), as a cream powder, m.p. 119°–121° C.; NMR (CDCl$_3$): 2.1(s, 3H), 5.0(s, 2H), 6.8–6.95(complex m, 8H), 7.2–7.55(complex m, 14H), 7.9–8.0(m, 1H).

(ii) A solution of compound (B) (41.8 g) in tetrahydrofuran (THF) (200 ml) was added over a period of 40 minutes to a suspension of lithium borohydride (4.1 g) in THF (400 ml) stirred at 0° C. under an atmosphere of argon. The mixture was stirred at ambient temperature for 20 hours and then cooled to 0° C. 20% Aqueous citric acid solution (40 ml) was added and the mixture was diluted with saturated sodium chloride solution (600 ml). The mixture was extracted with ethyl acetate (2×500 ml) and the extracts were washed with water (500 ml) and saturated sodium chloride solution (500 ml). The extracts were dried (MgSO$_4$) and volatile material removed by evaporation. The residue was purified by flash chromatography, eluting with ethyl acetate/hexane (2:3 v/v), to give 5-[2-(4'-hydroxymethylbiphenylyl)]-2-triphenylmethyl-2H-tetrazole (C) (17.4 g), as a white solid, m.p. 168°–169° C. (after recrystallisation from a mixture of ethyl acetate and hexane (1:9 v/v)); NMR (CDC13): 4.6(s, 2H), 6.85–7.0(m, 6H), 7.2–7.5(complex m, 16H), 7.9–8.0(m, 1H).

(iii) A solution of pyridine-sulphur trioxide complex (2.91 g) in DMSO (20 ml) was added over a period of 10 minutes to a stirred solution of compound (C) (3.0 g) and triethylamine (1.87 g) in DMSO (20 ml). The mixture was stirred for 1.5 hours and then carefully acidified to pH 5 by addition of 20% aqueous citric acid solution. Water (250 ml) was then added. The precipitated solid was collected by filtration, washed with water (4×100 ml) and hexane (4×100 ml), and dried under high vacuum to give 5-[2-(4'formylbiphenylyl)]-2-triphenylmethyl-2H-tetrazole (D) (2.28 g), as a white solid, m.p. 154°–156° C. (after recrystallisation from a mixture of ethyl acetate and hexane (1:1 v/v)); NMR (CDCl$_3$): 6.8–6.95(m, 6H), 7.15–7.45(complex m, 12H), 7.5–7.7(complex m, 4H), 80–8.1(m, 1H), 9.9(s, 1H).

iv) A 0.98M solution of methyllithium in ether (3.1 ml) was added to a stirred solution of compound (D) in THF (25 ml) at −50° C. under an atmosphere of argon. The solution was kept at −50° C. for 1 hour and then left to stand for 20 hours. Water (50 ml) was added and the mixture was extracted with ethyl acetate (2×30 ml). The extracts were washed with water (20 ml), saturated sodium chloride solution (20 ml) and dried (MgSO$_4$). Volatile material was removed by evaporation and the residue purified by flash chromatography, eluting with ethyl acetate/hexane (1:1 v/v), to give 5-[2-(4'-(1-hydroxyethyl)biphenylyl)]-2-triphenylmethyl-2H-tetrazole (E) 1.08 g), as a foam: NMR (d$_6$-DMSO): 1.2(d, 3H), 4.6–4.7(m, 1H), 5.1(d, 1H), 6.75–6.9(m, 6H), 7.0(d, 2H), 7.2(d, 2H), 7.25–7.4(complex m, 9H), 7.45–7.7(complex m, 3H), 7.8(dd, 1H).

(v) Sodium hydride (60% dispersion in mineral oil; 84 mg) was added to a stirred solution of compound (E) (1.05 g) in N,N-dimethylformamide (DMF) (15 ml). The mixture was stirred until evolution of hydrogen ceased and then 4-chloro-2-methylquinoline (370 mg) was added. The mixture was heated at 40° C. for 24 hours and then volatile material was removed by evaporation. The residue was partitioned between water (40 ml) and ethyl acetate (40 ml). The organic layer was separated, washed with saturated brine (20 ml) and dried (MgSO₄). Volatile material was removed by evaporation and the residue purified by flash chromatography, eluting with ethyl acetate/hexane (1:1 v/v), to give 2-methyl-4-[1-(2'-(2-triphenylmethyl-2H-tetrazol-5-yl)biphenyl-4-yl)ethoxy]quinoline (A) (400 mg), as a white powder, m.p. 160°–161° C. (after recrystallisation from a mixture of ethyl acetate and hexane (1:1 v/v)); NMR (d₆-DMSO): 1.5(d, 3H), 2.45(s, 3H), 5.8(q, 1H), 6.75–6.9(complex m, 8H), 7.1(d, 2H), 7.25–7.4(complex m, 11H), 7.45–7.75(complex m, 4H), 7.8–7.9(m, 2H), 8.2(dd, 1H).

EXAMPLE 2

Using an analogous procedure to that described in Example 1, but starting from 2-ethyl-4-[1-(2'-(2-triphenylmethyl-2H-tetrazol-5-yl)biphenyl-4-yl)ethoxy]-quinoline (A), there was obtained in 37% yield 2-ethyl-4-[1-(2'-(1H-tetrazol-5-yl)biphenyl-4-yl)ethoxy]quinoline hydrochloride, as a white solid, m.p. 176.5°–177.5° C.; NMR(d₆-DMSO): 1.4(t,3H), 1.8(d,2H), 3.1(q,2H), 6.2(q,1H), 7.15(d,2H), 7.4(s,1H), 7.5–7.75(complex m, 6H), 7.85(t,1H), 8.1(t,1H), 8.25(d,1H), 8.45(d,1H); mass spectrum (+ve FAB, DMSO/m-nitrobenzyl alcohol(NBA)): 422(M+H)⁺, 174; microanalysis, found: C., 68.2; H, 5.3; N, 15.5%; $C_{26}H_{23}N_5O \cdot HCl$ requires: C., 68.2; H, 5.2; N, 15.3%.

The starting material (A) was obtained in 60% yield as a foam; NMR(d₆-DMSO): 1.2(t,3H), 1.5(d,3H), 2.7(q,2H), 5.9(q,1H), 6.7–6.9(complex m, 8H), 7.1(d,2H), 7.25–7.4(complex m, 1H), 7.4–7.75(complex m, 4H), 7.8–7.9(m,2H), 8.2(dd,1H); using a similar procedure to that described in Example 1 but using 4-chloro-2-ethylquinoline instead of 4-chloro-2-methylquinoline in part (v).

EXAMPLE 3

(Note: All Parts by Weight)

The compounds of the invention may be administered for therapeutic or prophylactic use to warm-blooded animals such as man in the form of conventional pharmaceutical compositions, typical examples of which include the following:

| a) Capsule (for oral administration) | |
|---|---|
| Active ingredient* | 20 |
| Lactose powder | 578.5 |
| Magnesium stearate | 1.5 |
| b) Tablet (for oral administration) | |
| Active ingredient* | 50 |
| Microcrystalline cellulose | 400 |
| Starch (pregelatinised) | 47.5 |
| Magnesium stearate | 2.5 |
| c) Injectable Solution (for intravenous administration) | |
| Active ingredient* | 0.05–1.0 |
| Propylene glycol | 5.0 |
| Polyethylene glycol (300) | 3.0–5.0 |
| Purified water | to 100% |
| d) Injectable Suspension (for intramuscular administration) | |
| Active ingredient* | 0.05–1.0 |
| Methylcellulose | 0.5 |
| Tween 80 | 0.05 |
| Benzyl alcohol | 0.9 |
| Benzalkonium chloride | 0.1 |
| Purified water | to 100% |

Note: the active ingredient* may typically be an Example described hereinbefore and will conveniently be present as a pharmaceutically acceptable acid-addition salt, such as the hydrochloride salt. Tablets and capsules formulations may be coated in conventional manner in order to modify or sustain dissolution of the active ingredient. Thus, for example, they may be coated with a conventional enterically digestible coating.

Chemical Formulae

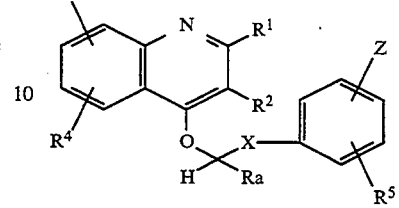

I

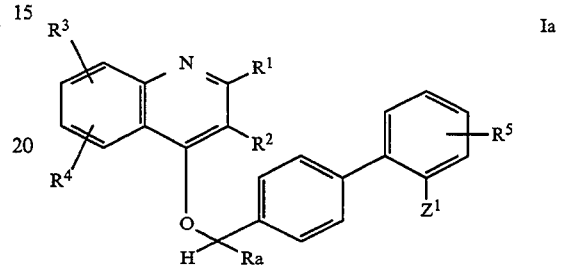

Ia

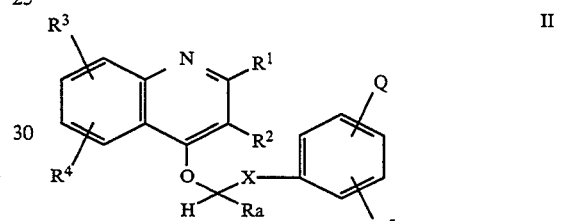

II

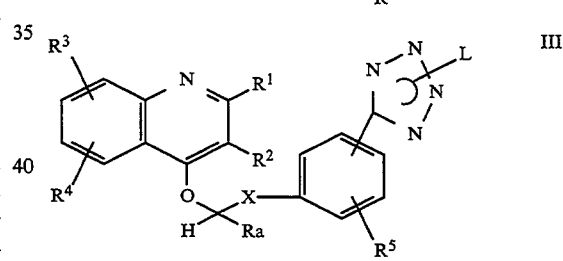

III

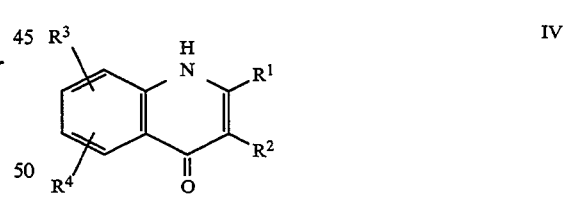

IV

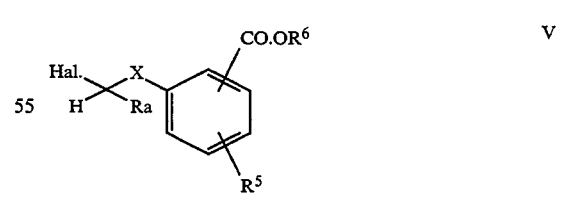

V

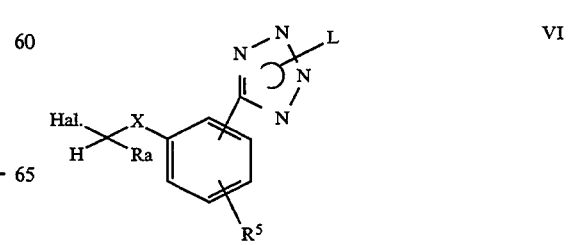

VI

-continued
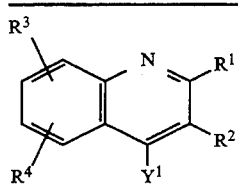
VII
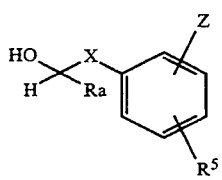
VIII
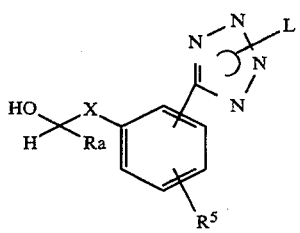
IX
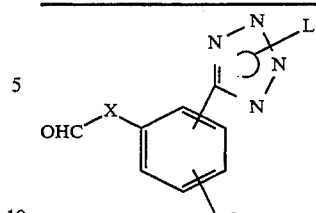
X
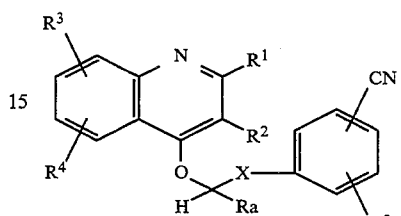
XI
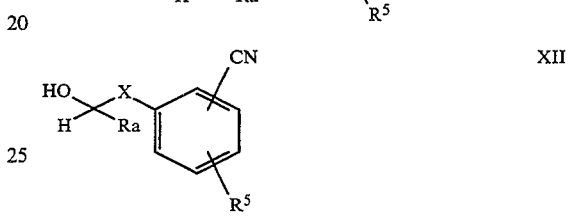
XII
Scheme 1
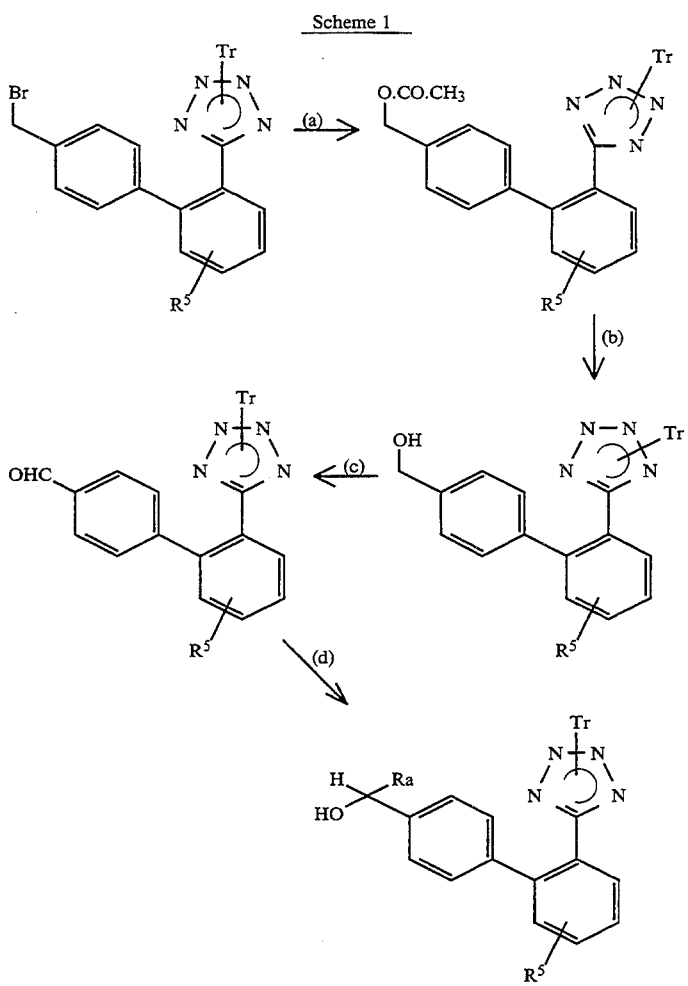
Note: Tr = triphenylmethyl (trityl)

Scheme 1 -continued

Reagents: (a) Potassium acetate, hexaoxacyclooctadecane, DME, reflux
(b) Lithium borohydride, THF, 0–25° C.
(c) Pyridine-SO₃ complex, Et₃N, DMSO, ambient temperature
(d) Ra.M, Et₂O/THF, −50° C. to ambient temperature

Scheme 2

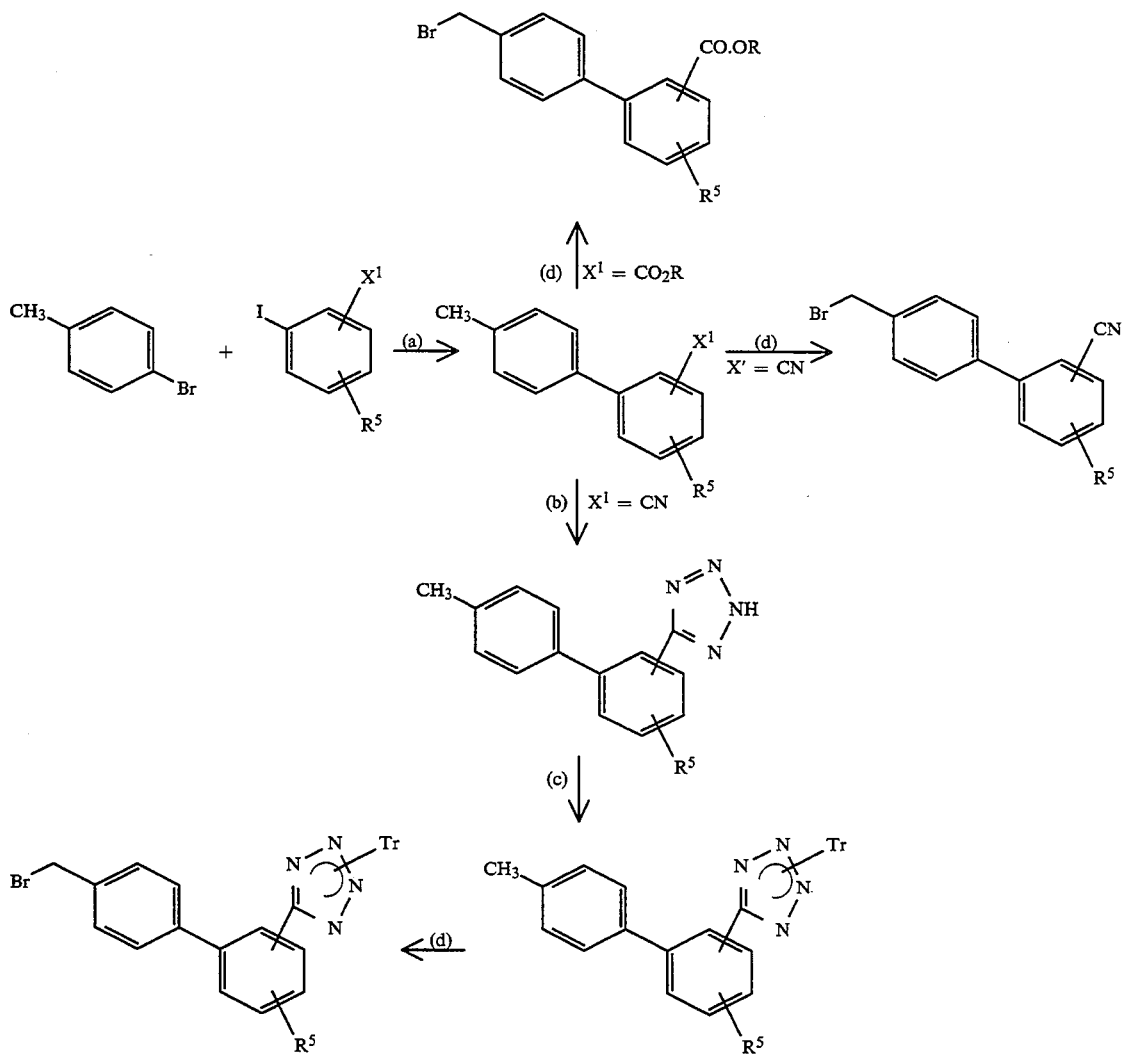

Note: R = lower alkyl, benzyl, phenyl; Tr = triphenylmethyl (trityl)

Reagents: a) BuLi/THF; ZnCl₂/Et₂O; Pd(Ph₃P)₄
b) Bu₃Sn.N₃/toluene; HCl/toluene
c) Tr.Cl/Et₃N/CH₂Cl₂
d) N-bromosuccinimide/azoisobutyronitrile/CCl₄

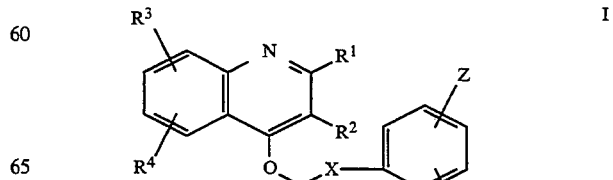

I

What we claim is:
1. A quinoline compound of the formula I wherein R¹ is hydrogen, (1-8C)alkyl, (3-8C)cycloalkyl, phenyl or substituted (1-4C)alkyl, the latter bearing one or more fluoro substituents or bearing a (3-8C)cycloalkyl, hydroxy, (1-4C)alkoxy or phenyl substituent; R² is hydrogen, R³ and R⁴ are independently selected from hydrogen, (1-4C)alkyl, (1-4C)alkoxy, fluoro(1-4C)alkoxy, halogeno, trifluoromethyl, cyano, nitro, hydroxy, amino, (1-4C)alkanoylamino, alkylamino and dialkylamino of up to 6 carbon atoms, dialkylamino-alkyl of 3 to 8 carbon atoms, (1-4C)alkanoyl, carbamoyl, N-alkylcarbamoyl and di-(N-alkyl)carbamoyl of up to 7 carbon atoms, carboxy, (1-4)alkoxycarbonyl, (1-6C)alkylthio, and substituted (1-4C)alkyl, the latter bearing an amino, hydroxy or (1-4C)alkoxy substituent; or R³ and R⁴ together form (1-4C)alkylenedioxy attached to adjacent carbon atoms of the benzene moiety of formula I; R⁵ is hydrogen, (1-4C)alkyl, (1-4C)alkoxy, halogeno, trifluoromethyl, cyano or nitro; X is phenylene optionally bearing a substituent selected from (1-4C)alkyl, (1-4C)alkoxy, halogeno, trifluoromethyl, cyano and nitro; Ra is (1-4C)alkyl optionally bearing one or more fluoro substituents; Z is 1H-tetrazol-5-yl, —CO.NH.(1H-tetrazol-5-yl) or a group of the formula —CO.OR⁶ or —CO.NH.SO₂.R⁷ in which R⁶ is hydrogen or a non-toxic, biodegradable residue of a physiologically acceptable alcohol or phenol, and R⁷ is (1-6C)alkyl, (3-8C)cycloalkyl or phenyl; and wherein any of said phenyl moieties may be unsubstituted or bear one or two substituents independently selected from (1-4C)alkyl, (1-4C)alkoxy, halogeno, cyano and trifluoromethyl; or a non-toxic salt thereof.

2. A compound as claimed in claim 1 wherein R¹ is hydrogen, methyl, ethyl, propyl, butyl, isobutyl, sec-butyl, pentyl, hexyl, cyclopropyl, cyclopentyl, cyclohexyl, phenyl, fluoromethyl, trifluoromethyl, 2,2,2-trifluoroethyl, pentafluoroethyl, hydroxymethyl, 1-hydroxyethyl, 2-hydroxyethyl, cyclopropylmethyl, cyclopentylmethyl, cyclohexylmethyl, 2-methoxyethyl, 2-ethoxyethyl, benzyl, 1-phenylethyl or 2-phenylethyl; R² is hydrogen, methyl, ethyl, propyl, butyl, isobutyl, sec-butyl, pentyl, hexyl, cyclopropyl, cyclopentyl, cyclohexyl, cyclopropylmethyl, cyclopentylmethyl, cyclohexylmethyl, 2-cyclopentylethyl, carboxy, methoxycarbonyl, ethoxycarbonyl, propoxycarbonyl, cyano, nitro, phenyl, benzyl, 1-phenylethyl or 2-phenylethyl; R³ and R⁴ are independently selected from hydrogen, methyl, ethyl, methoxy, ethoxy, trifluoromethoxy, 2-fluoroethoxy, 2,2,2-trifluoroethoxy, 3,3,3-trifluoropropoxy, fluoro, chloro, bromo, iodo, trifluoromethyl, cyano, nitro, hydroxy, amino, formamido, acetamido, propanamido, methylamino, ethylamino, butylamino, dimethylamino, diethylamino, dipropylamino, dimethylaminomethyl, 2-(dimethylamino)ethyl, 2-(diethylamino)ethyl, 3-(diethylamino)propyl, formyl, acetyl, butyryl, carbamoyl, N-methylcarbamoyl, N-ethylcarbamoyl, N,N-dimethylcarbamoyl, N,N-diethylcarbamoyl, carboxy, methoxycarbonyl, ethoxycarbonyl, propoxycarbonyl, methylthio, ethylthio, butylthio, methylsulphinyl, ethylsulphinyl, butylsulphinyl, methylsulphonyl, ethylsulphonyl, butylsulphonyl, hydroxymethyl, 1-hydroxyethyl, 2-hydroxyethyl, aminomethyl, 2-aminoethyl, 2-methoxyethyl and 2-ethoxyethyl; or R³ and R⁴ together form methylenedioxy or ethylenedioxy attached to adjacent carbon atoms of the benzene moiety of formula I; R⁵ is hydrogen, methyl, ethyl, methoxy, ethoxy, fluoro, chloro, bromo, iodo, trifluoromethyl, cyano or nitro; X is phenylene optionally bearing a substituent selected from methyl, ethyl, methoxy, ethoxy, fluoro, chloro, bromo, iodo, trifluoromethyl, cyano and nitro; Ra is methyl, ethyl, propyl, fluoromethyl, trifluoromethyl, 2,2,2-trifluoroethyl or pentafluoroethyl; R⁶ is hydrogen or a residue derived from a (1-6C)alkanol, or phenol or glycerol; and R⁷ is methyl, ethyl, propyl, isopropyl, butyl, pentyl, cyclobutyl, cyclopentyl, cyclohexyl or phenyl; and wherein any of said phenyl moieties may be unsubstituted or bear one or two substituents independently selected from methyl, ethyl, methoxy, ethoxy, fluoro, chloro, bromo, cyano and trifluoromethyl.

3. A compound of the formula Ia

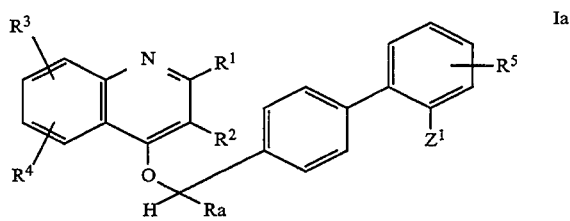

wherein R¹, R², R³, R⁴, R⁵, Ra have any of their meanings defined in claim 1 or 2; and Z¹ is carboxy or 1H-tetrazol-5-yl; together with the non-toxic salts thereof.

4. A compound as claimed in claim 1 or 3 wherein Z or Z¹ is 1H-tetrazol-5-yl and Ra is (1-4C)alkyl.

5. A compound I selected from 2-methyl-4-[1(2'-(1H-tetrazol-5-yl)biphenyl-4-yl)ethoxy]quinoline and 2-ethyl-4-[1-(2'-(1H-tetrazol-5-yl)biphenyl-4-yl)ethoxy]-quinoline; and the non-toxic salts thereof.

6. A salt as claimed in claim 1 which is selected from salts with acids forming physiologically acceptable anions and, for those compounds of formula I which are acidic, alkali metal, alkaline earth metal, aluminium and ammonium salts, and salts with organic bases affording physiologically acceptable anions.

7. A method for treating hypertension in a warm-blooded animal requiring such treatment which comprises administering to said animal a pharmaceutically effective amount of a compound of formula I, or a non-toxic salt thereof, as defined in claim 1.

8. A pharmaceutical composition which comprises an angiotensin II antagonistically effective amount of a compound of the formula I, or a non-toxic salt thereof, as claimed in claim 1, together with a pharmaceutically acceptable diluent or carrier.

9. A compound of the formula II

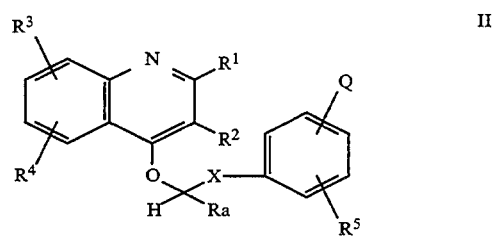

wherein R¹, R², R³, R⁴, R⁵, Ra and X have any of the meanings defined in claim 1, and Q is a protected carboxy group selected from (1-6C)alkoxycarbonyl, phenoxycarbonyl, benzyloxycarbonyl and carbamoyl.

10. A compound of formula III

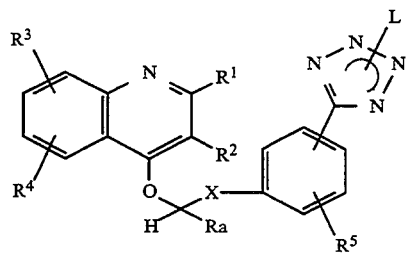
wherein $R^1$, $R^2$, $R^3$, $R^4$, $R^5$, Ra and X have any of the meanings defined in claim 1, and L is trityl or benzhydryl.
* * * * *